United States Patent [19]
Thall

[11] Patent Number: 5,880,813
[45] Date of Patent: *Mar. 9, 1999

[54] RETINAL DIAGNOSTIC DEVICE

[76] Inventor: Edmond H. Thall, 7208 Dukes Pl., Amarillo, Tex. 79109

[*] Notice: The term of this patent shall not extend beyond the expiration date of Pat. No. 5,751,395.

[21] Appl. No.: 972,104

[22] Filed: Nov. 17, 1997

Related U.S. Application Data

[63] Continuation of Ser. No. 781,667, Jan. 10, 1997, Pat. No. 5,751,395.

[51] Int. Cl.$^6$ ........................................................ A61B 3/00
[52] U.S. Cl. ........................... 351/221; 351/206; 351/246
[58] Field of Search ..................................... 351/221, 206, 351/246, 205, 214, 215

[56] References Cited

U.S. PATENT DOCUMENTS

| | | | |
|---|---|---|---|
| 4,272,165 | 6/1981 | Muchel et al. ............................... | 351/13 |
| 4,721,378 | 1/1988 | Volk ......................................... | 351/205 |
| 5,090,416 | 2/1992 | Ogino et al. ............................ | 128/691 |
| 5,255,025 | 10/1993 | Volk ........................................ | 351/205 |
| 5,268,711 | 12/1993 | Poxleitner et al. ...................... | 351/214 |
| 5,430,509 | 7/1995 | Kobayashi ............................... | 351/221 |
| 5,485,229 | 1/1996 | Hare ......................................... | 351/215 |
| 5,751,395 | 5/1998 | Thall ........................................ | 351/221 |

OTHER PUBLICATIONS

Tasman, "Duane's Clinical Ophthalmology," vol. 1, Rev. Ed. 1996, pp. 1–21.

Lipson et al., Optical Physics, Third Edition, Chapter Twelve, "Image formation," Cambridge University Press, pp. 327–382.

*Primary Examiner*—Hung Xuan Dang
*Attorney, Agent, or Firm*—Fulwider Patton Lee & Utecht, LLP

[57] ABSTRACT

An ophthalmological diagnostic system and method providing improved resolution and enhanced visualization of internal anatomical structures of the eye. The optical transform of light reflected and scattered by the internal anatomical structures of the eye is modified to selectively provide dark field, phase contrast and fourier filtered images, and also to provide interference patterns of difficult to visualize transparent or translucent internal structures of the eye such as the nerve fiber layer of the retina.

26 Claims, 9 Drawing Sheets

RETINAL DIAGNOSTIC DEVICE

This is a continuation of application Ser. No. 08/781,667, filed Jan. 10, 1997 now U.S. Pat. No. 5,751,395.

BACKGROUND OF THE INVENTION

1. Field of the Invention

The invention relates generally to medical instruments for examining the anatomy of the eye, and more particularly to an improved apparatus and method for visualizing translucent or transparent internal anatomical structures at the back of the eye.

2. Description of the Related Art

In-vivo examination of the retina of the eye is routinely performed during ophthalmological examinations because small changes in the condition of the retina are often indicative of the onset of several sight threatening diseases, such as glaucoma, diabetes, cystoid macular edema, age related macular degeneration, subretinal neovascular membranes, retinal edema arising as a result of various vascular diseases and diseases of the cranial nerves. For example, detectable changes in the condition of the optic nerve head may reflect the loss of retinal ganglion cell axons, which has been found to occur in the early stages of glaucoma. Similarly, changes in the neuroretinal rim and the optic disk may also be correlated with changes in vision during the course of an ocular disorder.

Degenerative diseases of the retina, or changes in the retina due to glaucoma, may be quantitatively evaluated using various methods, such as tonometry, visual field analysis and other techniques. Photographic techniques, coupled with computer enhancement of the resulting photographs may also be used to document the condition of the retina. While these methods provide valuable information about the gross anatomy and general condition of the retina, they lack the sensitivity or resolution necessary to resolve the fine structure of the retina, such as the nerve fiber layer. The ability to view the nerve fiber layer, and to be able to detect and measure changes in its structure and thickness, is important in diagnosing the onset and course of glaucoma.

Because glaucoma affects a large number of people and produces serious visual loss, a wide variety of diagnostic equipment and techniques have been utilized to view the nerve fiber layer of the retina. Most of the techniques currently used to evaluate the retina utilize a device known as the ophthalmoscope to observe the retina. Using the ophthalmoscope, a physician visualizes the retina, and, using a camera or optoelectronic imaging tube, records an image of the retina. Where the image is electronically obtained, the electronic signals comprising the image may then be processed using a computer and image enhancing software to enhance the structural details of the retina that are present.

In indirect ophthalmoscopy, examination of the retina of the eye is performed by observing a real aerial image of the retina. Various optical systems have been developed to generate the real aerial image of the retina. Typically, an ophthalmoscope consists of a light source and a combination of optical elements adapted to transmit light from the light source onto the retina and then to transmit any light scattered by the structures of the eye back to the observer for viewing and recording. For example, one system uses an objective lens to converge light from an ophthalmoscope light source onto the retina and also to form the aerial image. One problem with all of the techniques employing the ophthalmoscope is that only retinal and ocular structures capable of scattering light back into the optical elements of the ophthalmoscope are visible. Transparent or translucent structures of the eye, such as the nerve fiber layer, scatter very little of the light provided by the ophthalmoscope's light source, and so are extremely difficult to visualize.

One approach used to increase the sensitivity of the ophthalmoscope has been to increase the amount of light scattered by translucent structures such as the nerve fiber layer by increasing the amount of the light supplied by the light source. The disadvantage of this approach is that the retina is extremely sensitive to light, and can suffer permanent damage if the light provided by the light source is too intense. Thus, the maximum intensity of the light supplied by the light source of the ophthalmoscope is limited by the requirement that no damage be caused to the eye during the diagnostic procedure. Unfortunately, the amount of light scattered by the nerve fiber layer, even with the light source providing light at its maximum safe intensity, is often too small to allow visualization of subtle changes in the nerve fiber layer that are valuable in diagnosing glaucoma. Moreover, the increased intensity of light provided to the eye also results in increased scattering of the light by other structures of the eye that further obscures the detail of the nerve fiber layer by overwhelming the small percentage of the scattered light that is actually reflected by the nerve fiber layer.

Several methods have been proposed to improve nerve fiber layer visibility by increasing the relative amount of light scattered by the nerve fiber layer compared to other ocular structures. One approach has been to illuminate the retina with light having a wavelength that is preferentially scattered by the nerve fiber layer and which is not scattered by other ocular structures. One such method interposed a green filter between the light source of the ophthalmoscope and the eye, but has been unsuccessful in obtaining images with enough resolution to view the nerve fiber layer because there is only a small difference in the scattering of light between the nerve fiber layer and other ocular structures at the wavelength of light transmitted by the green filter.

Another approach utilized polarized light in an attempt to increase the relative scatter of the light by the nerve fiber layer based on the theory that the nerve fibers, being long thin cylinders, should be strongly birefringent. This approach was also unsuccessful in significantly improving the visualization of the nerve fiber layer because the nerve fiber layer proved to be only weakly birefringent; thus the expected increase in scattered light by the nerve fiber layer in relation to non-birefringent structures of the eye was not obtained.

Alternative approaches that do not directly visualize individual nerve fibers but instead measure some anatomical feature of the nerve fiber layer have also been attempted. Ellipsometry, which can be used to estimate the thickness of the nerve fiber layer by measuring the degree of birefringence of the nerve fiber layer, is one such method. Using ellipsometry, it is possible to determine the birefringence of the nerve fiber layer at several points on the surface of the retina. The thickness of the nerve fiber layer may then be calculated from these measurements since the degree of birefringence is dependent upon the thickness of the layer. However, the resolution of this technique is limited because the other structures of the eye are significantly more birefringent than the nerve fiber layer; light scattered by these structures interferes with the measurement and reduces its accuracy. Thus, this method can only measure relatively large differences in the thickness of the nerve layer, and is incapable of detecting the subtle changes in nerve fiber layer thickness caused by glaucoma.

Several methods have been used to produce cross-sectional images of the retina in an attempt to detect changes in the nerve fiber layer. One such method is confocal scanning laser ophthalmoscopy. While this method is capable of producing cross-sectional images of the nerve fiber layer, the images produced do not have sufficient resolution to enable detection of small changes in the thickness of the nerve layer. Another method capable of producing cross-sectional views of the retina is coherence domain tomography, also known as laser doppler interferometry. In theory, this method should be capable of estimating the thickness of the nerve fiber layer with an accuracy of ten microns, but is adversely affected by the amount of light scattered intraretinally by the nerve fiber layer. As a practical matter, this method is useful for detecting retinal defects extending through the full thickness of the retina, but has not provided the accuracy needed to monitor changes in the thickness of the nerve fiber layer caused by glaucoma. In addition to the specific disadvantages discussed above, ellipsometry, confocal laser ophthalmoscopy and coherence domain tomography are all incapable of visualizing individual nerve fibers in the nerve fiber layer.

When an image of the retina has been obtained and stored using optoelectronic means, as discussed above, or where a photograph of an image has been digitized, the image may be processed using specialized computer software to enhance the details of the image. The degree to which a stored image can be enhanced, however, depends on the quality and detail of the original image. Where the original image contains little information, as in the case where little light is scattered by the nerve fiber layer, image processing is typically of little value.

What has been needed, and heretofore unavailable, is an accurate and reliable apparatus and method for visualizing individual nerve fibers in the retina and for measuring the thickness of the nerve fiber layer to a high degree of accuracy without requiring unsafe or uncomfortable levels of illumination.

SUMMARY OF THE INVENTION

Briefly, and in general terms, the present invention provides a diagnostic system and a method of using the system for visualizing transparent and translucent internal anatomical structures of the eye. Basically, the apparatus comprise a novel arrangement of optical elements for modifying the optical transform of an image formed from light reflected or scattered by the internal structures of the eye. This arrangement of optical elements may be easily changed as required by a user to tailor the modified optical transform to enhance selected internal structures of the eye.

More specifically, in a presently preferred embodiment, by way of example and not necessarily by way of limitation, the diagnostic system has an illumination system that can be adjusted to provide either a real or a virtual image of a spatial filter. This light forming this image is transmitted into the eye of a patient where it is scattered back out of the eye by the internal anatomical structures of the eye into a viewing system. An optical element having an opaque spot located in the center of the element is placed in the path of the scattered light. This opaque spot obscures the central maximum of the beam of scattered light such that the image formed in the image plane of the viewing system comprises only light rays that are not obscured by the opaque spot. This dark field image provides increased resolution of internal anatomical structures of the eye, such as the nerve fiber layer of the retina, that do not scatter light strongly.

In another aspect, the present invention modifies the optical transform of the image of the internal structures of the eye by placing a filter comprising a phase plate and a centrally located semi-opaque dot in the plane of the virtual image of the spatial filter of the illumination system. This arrangement provides a phase contrast image of the internal structures of the eye, which may be advantageous in selectively viewing transparent and translucent structures of the eye at the expense of reduced resolution of ocular structures that strongly scatter incident light.

In yet another aspect, a fourier filter may be used to modify the optical transform. With this arrangement, the diameter of the transparent annular area may be adjusted to selectively enhance certain internal structures of the eye. This technique is advantageous in providing superior resolution of a specific anatomical structure, although other details adjacent to the specific structure will not be resolved. A series of annuli may also be used to provide a series of discreet ranges of structure sizes that may be viewed. The fourier filter may also be combined with a phase plate to provide a fourier filtered phase contrast image.

In still another aspect of the invention, the light from the illumination system of the diagnostic system is transmitted through a polarizing lens, a polarizer analyzer and a wollaston prism into the eye. The light reflected and scattered from the internal structures of the eye traverses back through the wollaston prism, the polarizer analyzer and the polarizing lens into the viewing system. This arrangement modifies the optical transform of the image to produce a lateral shear interference pattern. This arrangement is provides selectively enhances the visualization of structures that reflect or scatter light in a specular manner and suppresses light that is diffusively reflected or scattered.

These and other features and advantages of the invention will become apparent from the following detailed description when taken in conjunction with the accompanying exemplary drawings.

DETAILED DESCRIPTION OF THE PREFERRED EMBODIMENTS

Figure 1:
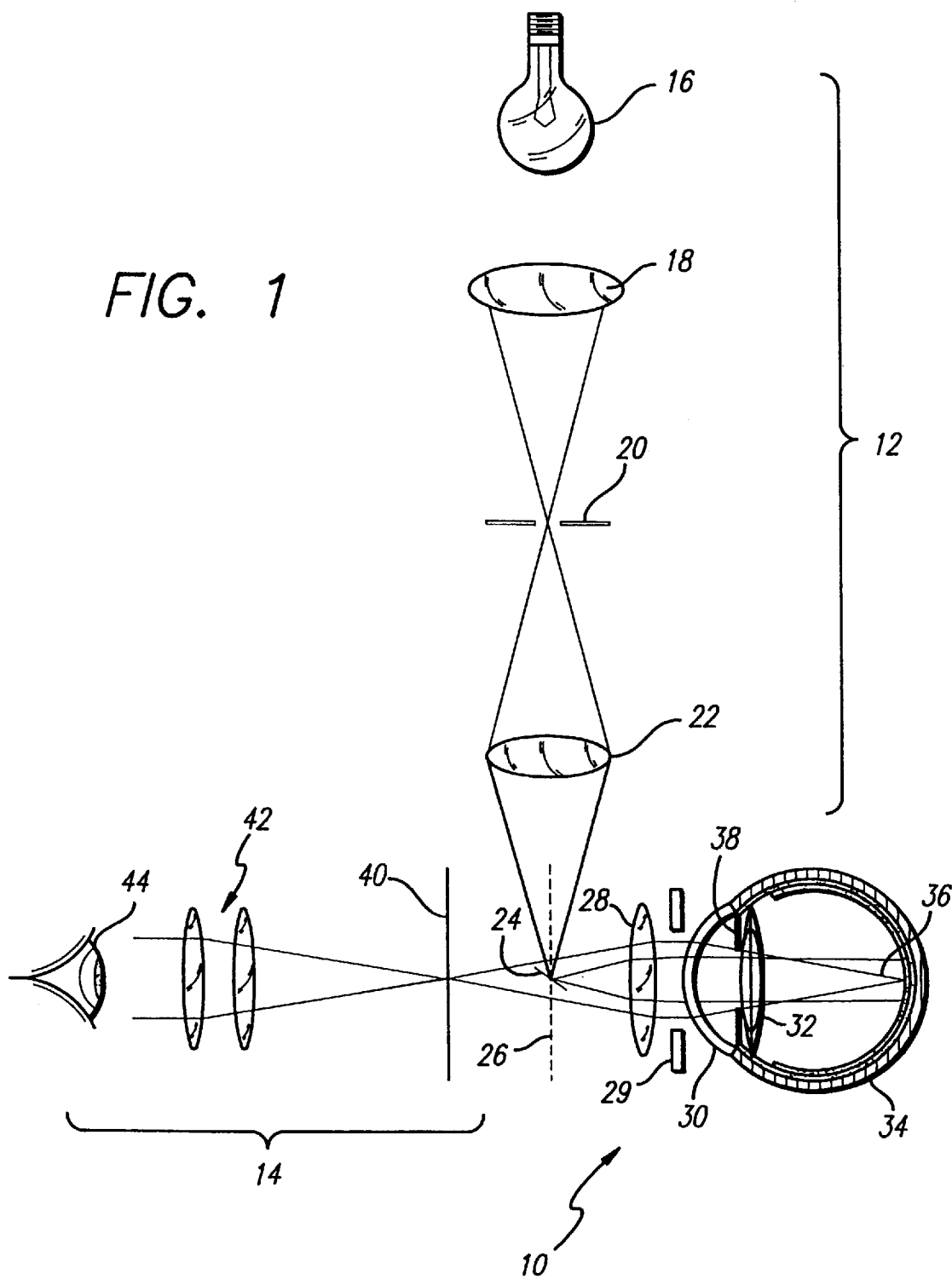
FIG. 1 is a schematic diagram, partially in section, showing one embodiment of the invention as it would be used during examination of a patient.

Referring now to the drawings in more detail, wherein like referenced numerals refer to like or corresponding elements among the several drawings, there is shown in FIG. 1 a system for observing the internal anatomical structures of the eye generally indicated as reference numeral 10. The system 10 consists of an illumination system generally indicated by numeral 12 and a viewing system 14.

The illumination system 12 comprises a light source 16 for providing light rays that are focused by a condensing lens 18 onto a spatial filter 20. Light rays passing through the spatial filter 20 are then focused by a second condensing lens 22 onto a reflector 24 which deflects the light rays through an ophthalmoscopic lens 28 and an adjustable iris 29 into a patient's eye 34.

The ophthalmoscopic lens 28 and the iris 29 may be separate optical elements, or the ophthalmoscopic lens 28 and adjustable iris 29 may be combined into a single assembly. Furthermore, the ophthalmoscopic lens 28 may comprise a number of individual lenses. The ophthalmoscopic lens 28, or the adjustable iris 29, where such an iris is used, may be positioned on or adjacent to the cornea 30 of the eye 34 to compensate for the refraction of the reflected light rays by the cornea 30 and the crystalline lens 32. This compensation is often necessary to ensure that the light rays transmitted into the eye through the cornea 30 and crystalline lens 32 are essentially parallel when they fall upon the fundus of the retina 36. Light rays falling upon the structures of the retina 36 are scattered by those structures back out of the eye into the viewing path. The scattered light rays form an image of the retina 36 in image plane 40 which is viewed by an observer 44 through the viewing system 14. The viewing system 14 may comprise one or more lenses 42 or other optical elements, such as filters or quarter wave plates, to form a modified optical transform of the image created by the light scattered by the internal anatomical structures of the eye and for conditioning and focusing the light rays passing through the image plane 40 to improve the visualization of the imaged retinal structures.

Typically, the pupil 38 of the eye is pharmacologically dilated during examination of the internal structures of the eye to maximize the amount of light incident upon the internal structures of the eye 34 and to provide the widest viewing area possible. In some cases, however, peripheral off-axis pathology present in the eye 34 limits the view of the internal structures of the eye 34, and a widely dilated pupil 38 may further interfere with the view. The inclusion of the adjustable iris 29 allows the examiner to adjust the viewing aperture to maximize the visibility of the transparent and translucent internal anatomical structures of the eye 34.

Additionally, surgery to remove a cataractous crystalline lens 32 is common among elderly patients. During this type of surgery, the cloudy contents of the crystalline lens 32 are removed, typically leaving a bag-shaped tissue called the posterior capsule in which is implanted an intraocular lens. Fairly frequently, however, the posterior capsule opacifies following surgery, and a laser is typically used to form small openings in the opacified posterior capsule. Typically, these small openings are located along the optical axis of the eye 34, and are slightly larger than the patient's normal, undilated, pupil size. When such a patient's eye is dilated to perform an examination of the internal structures of the eye 34, light traversing the opacified posterior capsule adds to the amount of light scattered within the eye, and reduces the resolution and visualization of the transparent and translucent internal structures of the eye 34, such as the retina 36. It is thus advantageous to include the adjustable iris 29 in the system 10 to allow the examiner to narrow the diameter of the beam of light from the illumination system 12 to a diameter less than the diameter of the opening in the opacified posterior capsule. This essentially eliminates the interference caused by light scattered as it traverses the opacified portion of the posterior capsule.

The reflector 24 is located so that it is positioned within the optical transform plane 26 of the condensing lens 22. In this position, the reflector is also located in the viewing path of the light scattered by the retina 36. The reflector 24 may be sufficiently small in size so that it blocks the passage of light rays comprising the area of maximum optical intensity of the light that is scattered from the retina 36 back through lens 28, but allows passage of light rays in the periphery of the scattered beam of light. The size of the reflector 24 may be adjusted to block more or less of the light rays comprising the area of maximum intensity of the scattered light beam dependent upon the requirements of the designer of the system.

Because the central area of maximum intensity of the scattered light beam has been blocked by the reflector 24, a modified optical transform image of the retina 36 is formed at the image plane 40. This modified optical transform image results in improved contrast and visualization of the translucent structures of the retina 36.

Figure 2:
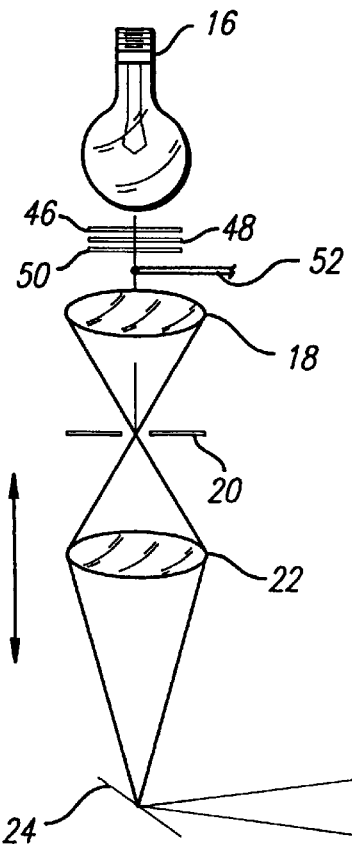
FIG. 2 is an enlarged partial schematic diagram of the illumination system of the embodiment depicted in FIG. 1.

As illustrated by FIG. 2, the beam of light rays produced by light source 16 may be directed through a series of filters before being focused by condensing lens 18 onto the spatial filter 20. More specifically, it will be apparent that any light source may be used to provide illumination for the illumination system 12, such as an incandescent bulb, fluorescent bulb, arc light, gas discharge tube, or laser. Filters 46, 48, and 50 may be inserted into the optical path between the light source 16 and the condensing lens 18 to condition the light before it is focused by the condensing lens 18 on to the spatial filter 20. For example, filter 46 may be a partially transmitting filter to reduce the intensity of light rays passing through it to maintain the intensity of the beam of light that will ultimately be directed into the eye at a safe level to prevent harm to the retina 36 or other structures of the eye 34. Alternatively, filter 46 may preferentially absorb certain wavelengths of light and transmit other wavelengths of light to eliminate potentially harmful wavelengths of light.

Filter 48 may be a polarizing filter capable of providing linear, circular, or elliptical polarization of the beam of light produced by the light source 16. Filter 48 may be easily changeable within the illumination system 12 so that the beam of light produced by light source 16 traversing filter 48 may be linearly polarized, circularly polarized, or elliptically polarized as desired by the observer to enhance the visualization of the structures of the retina 36.

Filter 50 may be a band pass filter such that only selected wavelengths of light are transmitted, while all other wavelengths of the light are absorbed. It will be understood by those skilled in the art that filter 50 may be a partially transmitting filter such as was described previously in relation to filter 46. It will also be understood that filters 46, 48 and 50 may be arranged in any order, or that one or more of the filters 46, 48 and 50 may be omitted dependent upon the characteristics of the light beam that are desired, the type of image to be formed and the analysis to be performed.

In a preferred embodiment of the present invention, a photodetector 52 is located in the beam of light produced by the light source 16 and the condensing lens 18. The photodetector 52 detects the intensity of the beam of light after the beam of light has passed through filters 46, 48, and 50, and may be operable provide a signal to the operator of the instrument indicating that the intensity of the beam of light is at a potentially unsafe level. Alternatively, the signal from the photodetector 52 may cooperate with the power supply of the light source 16 to either interrupt or to adjust the power supply to the light source 16 to extinguish the light source 16 or reduce the intensity of the light beam produced. In another embodiment, one of the filters 46, 48 and 50 may be an optoelectric device capable of altering its transmission characteristics in response to the signal of the photodetector 52. In this manner, the photodetector 52 prevents injury to the retina 34 of a patient due to damage to filters 46, 48, and 52 caused by rough handling of the illumination system 12 and/or deterioration of the various elements of the illumination system 12.

The spatial filter 20 has a small aperture 21 of varying diameter. The spatial filter 20 absorbs all of the light rays from the condensing lens 18 except those rays that pass through the aperture 21. As shown in FIG. 2, the condensing lens 22 may be moved closer or farther away from reflector 24 to focus the beam of light passing through the spatial filter 20 onto the reflector 24, forming a real image of the spatial filter 20 on the reflector 24. While the condensing lens 22 is depicted as a single optical element, the condensing lens 22 may also be an assembly comprising several optical elements, such as a combination of lenses, filters or other optical devices, to provide the desired focusing and conditioning of the light beam.

In a preferred embodiment of the system 10, the individual elements of the illumination system 12 and the viewing system 14 may be mounted in several tubes or other structures to prevent unwanted external light from interfering with the beam of light provided by light source 16. These tubes or other structures may be mounted such that the tubes extend from the body of the system 10. Moreover, the tubes may be adjustably mounted on the body of the system 10 so that the illumination system 12 may be translated so that the reflector 24 may be positioned at selected locations relative to the optical transform plane of the condensing lens 22. Alternatively, the entire system 10 may be mounted in a single enclosure.

The arrangement of the various elements of the system 10 described may also be capable of various adjustments as are well know to those skilled in the art to alter the orientation and alignment of the various optical elements of the illumination system 12 and the viewing system 14. The devices enabling such adjustments may be actuated either manually by the viewer 44 manipulating the adjusting devices or remotely where the devices are controlled using appropriate servo mechanisms. Additionally, the devices may be actuated by signals provided by a computer in response to commands input into the computer by the viewer 44.

Figure 3:
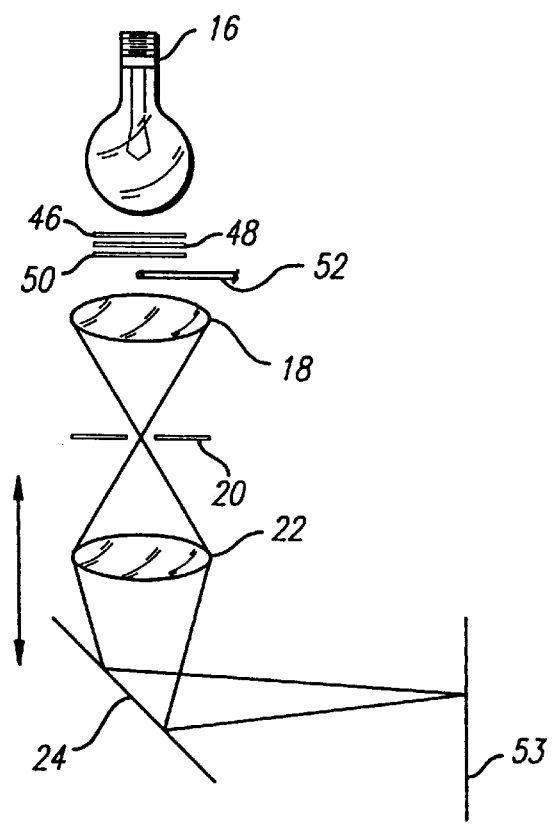
FIG. 3 is an enlarged partial schematic diagram of the illumination system of FIG. 1 showing the positioning of the reflector to provide a real aerial image of the spatial filter.

Referring now to FIG. 3, an alternative embodiment of the illumination system 12 is depicted wherein the reflector 24 is positioned above the optical transform plane 26 of the condensing lens 22. When the reflector 24 is in this position, a real image of the spatial filter 20 is formed by the reflector 24 at image plane 53. Depending on the position of reflector 24 relative to condensing lens 22, the image plane 53 may be located at various positions between the reflector 24 and the ophthalmoscopic lens 28 (FIG. 1). In this manner, variations in the refractive characteristics of the eye due to either the physical dimensions of the eye 34 or the optical structures of the eye, such as the cornea 30 and the crystalline lens 32 may be accommodated.

Figure 4:
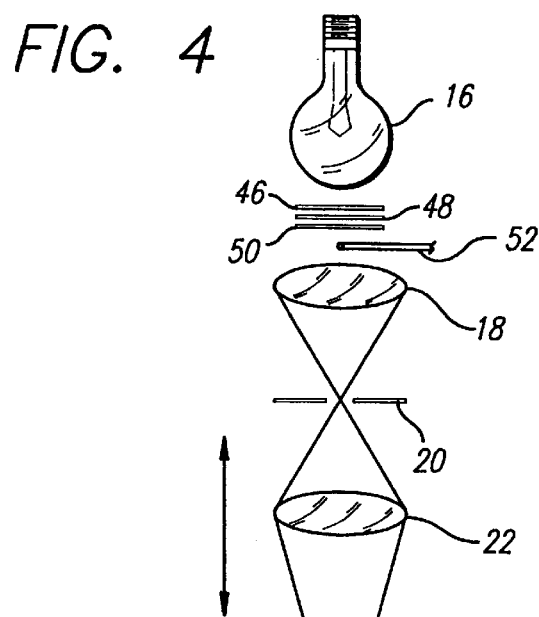
FIG. 4 is an enlarged partial schematic diagram of the illumination system of FIG. 1 showing the positioning of the reflector to provide a virtual image of the spatial filter.

FIG. 4 depicts another embodiment of the illumination system 12 where the reflector 24 is positioned such that a real image of the spatial filter 20 is formed between the reflector 24 and the condensing lens 22. In this arrangement, a virtual image of the spatial filter 20 is formed behind the reflector 24 in the viewing path. This arrangement is advantageous in that the optical transform of the light reflected into the viewing system 14 may be modified after it traverses the reflector 24.

Figure 5:
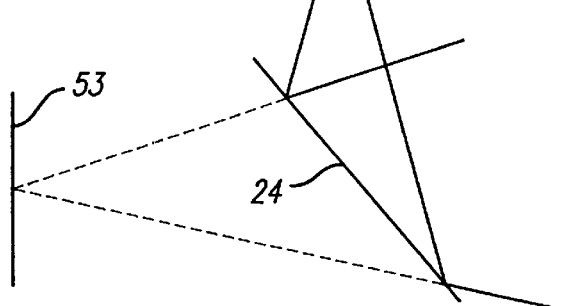
FIG. 5 is a schematic diagram of another embodiment of the illumination system.
Figure 5:
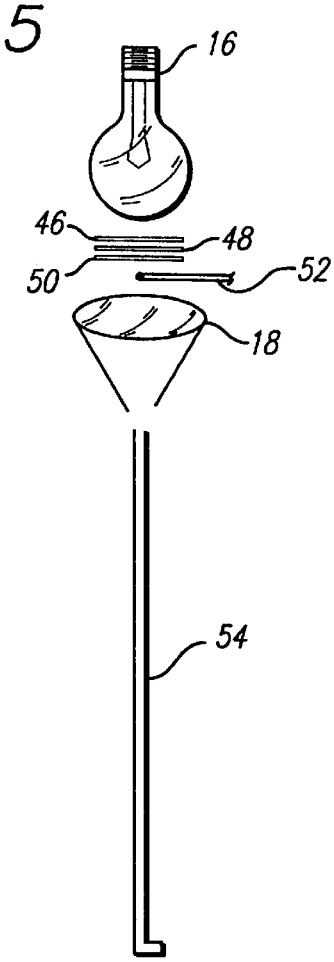

Referring now to FIG. 5, an embodiment of the illumination system 12 is depicted wherein the light beam from light source 16 is focused by the condensing lens 18 into the end of a flexible fiber optic element 54. Since the fiber optic element 54 is flexible, the end of the fiber optic element may be positioned so that light exiting the fiber optic element 54 is transmitted along an axis different from the light entering the fiber optic element 54. This arrangement eliminates the need for the reflector 24, and focusing of the light incident upon the ophthalmoscopic lens 28 may be obtained by changing the position of the end of the fiber optic element 54 relative to the ophthalmoscopic lens 54 using means well know to those skilled in the art.

Figure 6:
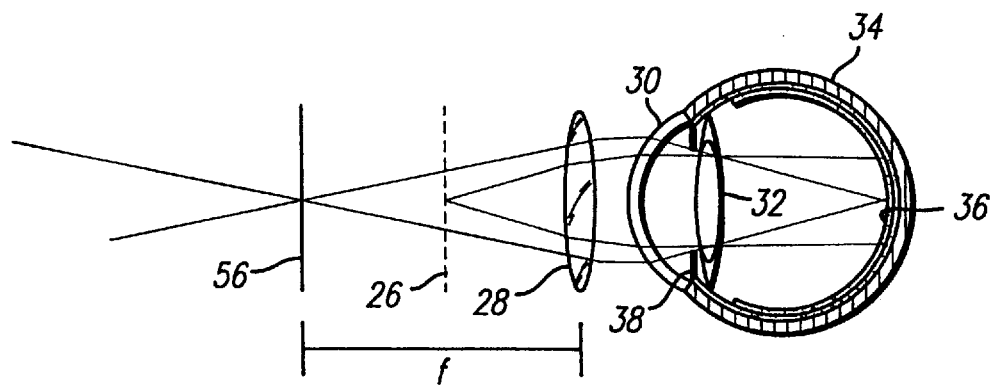
FIG. 6 is a schematic diagram, partially in section, of an embodiment of the illumination system utilizing a non-contact ophthalmoscopic lens.

Referring now to FIG. 6, the typical relationship between the ophthalmoscopic lens 28, image plane 56, and the optical transform plane 26 is depicted. In order to focus the beam of light from the illuminating system 12 upon the fundus of the retina 36 or other internal anatomical structures of the eye 34, the optical elements of the illuminating system 12 must provide either a point source of illumination, such as that depicted in FIGS. 1 and 2, a real image as depicted in FIG. 3 or a virtual image of the point source as depicted in the FIG. 4 or as provided by the fiber optic system of FIG. 5, at a position in the optical transform plane 26. By positioning the point source 58 in the optical transform plane 26, the rays of light emerging from the point source will be refracted by the ophthalmoscopic lens 28, the cornea 30, and the crystalline lens 32 such that the rays of light emanating from the point source 58 are parallel or nearly so when the rays of light are incident upon the retina 36. This is accomplished by positioning the point source 58 within the focal length f of the ophthalmoscopic lens 28. In this arrangement, the image plane 56 will coincide with the focal plane of the ophthalmoscopic lens 28. It will be apparent to those skilled in the art that the positions of the image plane 56 and the optical transform plane 26 will vary as a function of the refractive error of the eye 34.

Figure 7:
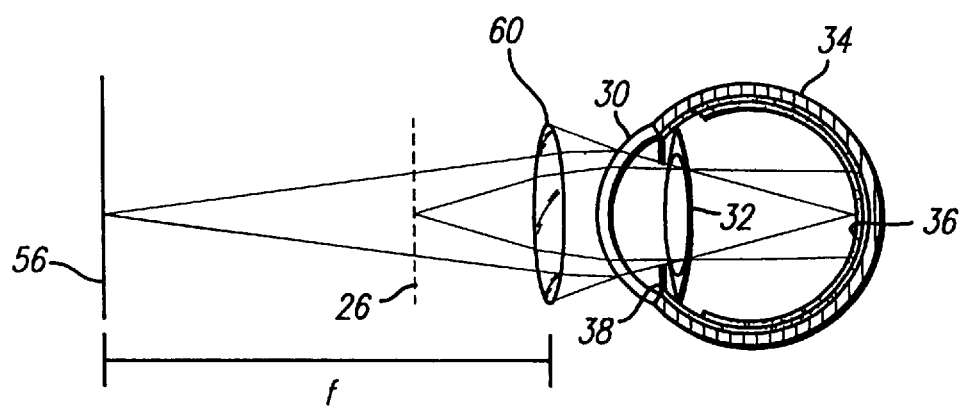
FIG. 7 is a schematic diagram of another embodiment of the illumination system utilizing an ophthalmoscopic lens in contact with the cornea of the eye.

Alternatively, as depicted in FIG. 7, it is common to utilize a contact lens 60 rather than the ophthalmoscopic lens 28 to transmit the light beam from point source 58 into the eye 34 of the patient. Such contact lenses have a larger focal length f than the corresponding ophthalmoscopic lens 28. Use of such a contact lens 60 also results in increased resolution of the images at the image plane 56 and helps to eliminate aberrations of the transmitted images caused by the cornea 30 of the eye 34.

Figure 8:
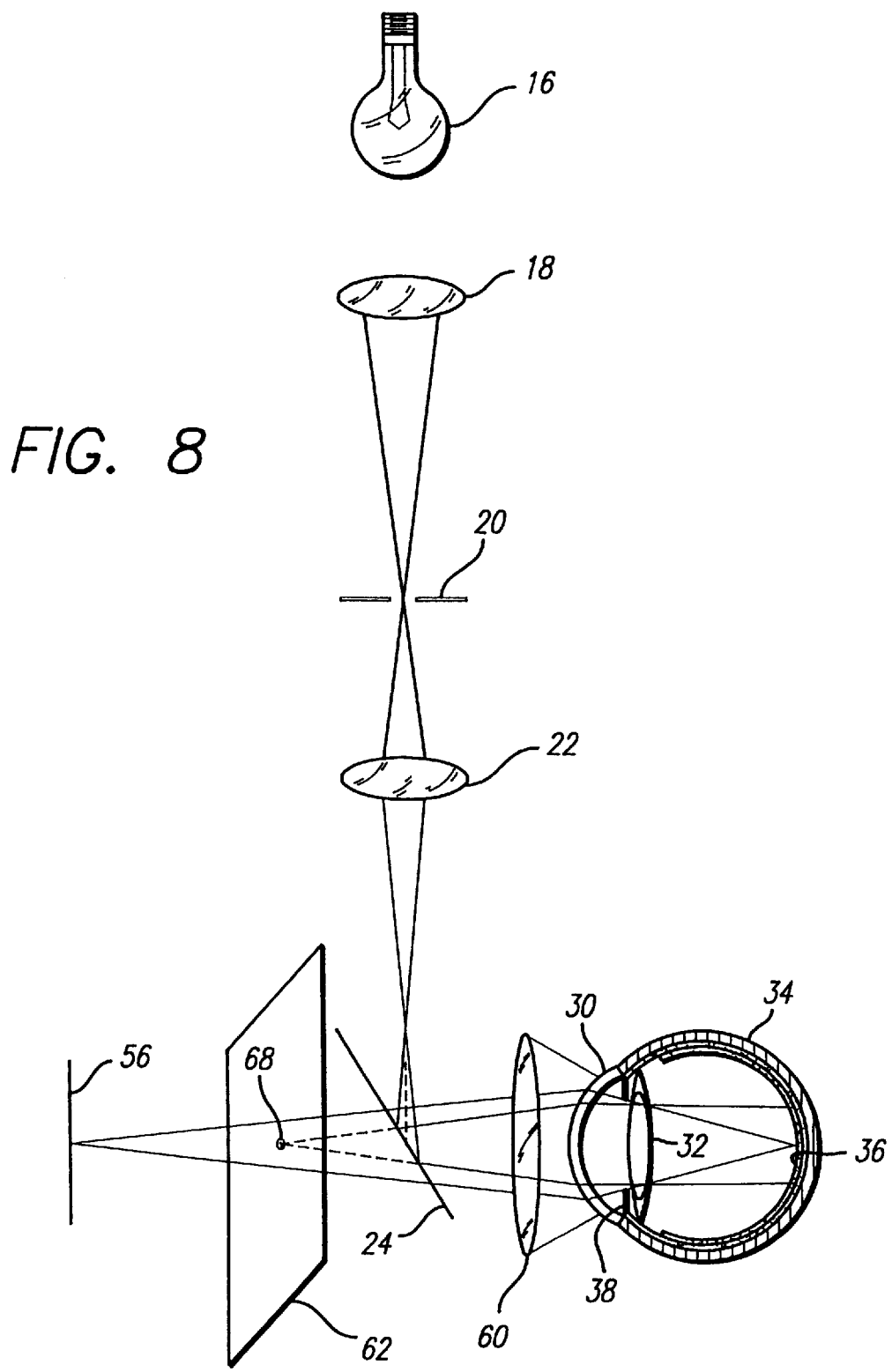
FIG. 8 is an enlarged partial schematic diagram of one embodiment of the invention illustrating the arrangement of optical elements necessary to modify the optical transform of the image to provide a dark field image.

FIG. 8 illustrates an embodiment of the present invention wherein the optical transform plane 62 is modified to provide a dark field image. In this embodiment, the beam of light transmitted by the spatial filter 20 is focused in front of the reflector 24 by the condensing lens 22. As described previously in relation to FIG. 4, this arrangement results in the formation of a virtual image of the spatial filter 20 on a glass plate 62 placed in the image plane. An opaque dot 64 on the glass plate 62 is positioned at the location of the virtual image of the spatial filter 20 formed on the glass plate 62. Scattered light reflected back from the retina 36 along the viewing path will pass through the glass plate 62. As it passes through the glass plate 62, a portion of the scattered light beam will be absorbed by the dot 64, thus modifying the optical transform of the image, before forming a real image of the retina 36 at image plane 56. Because a portion of the scattered light is absorbed by the dot 64, the image of the retina 36 will be formed only from the annulus of light passing through the glass plate 62 that is not absorbed by the dot 34. By removing the central, most intense scattered light, the contrast and resolution of the image of the retina 36 formed from the remaining scattered light is enhanced. One advantage of this embodiment of the invention is that it provides visualization of structures that are both strong and weak scatters of light. This allows the viewer 44 to orient his observation of the image using familiar, strongly scattering structures of the eye 34 to locate more difficult to visualize weakly scattering transparent or translucent structures of the eye 34.

Figure 9:
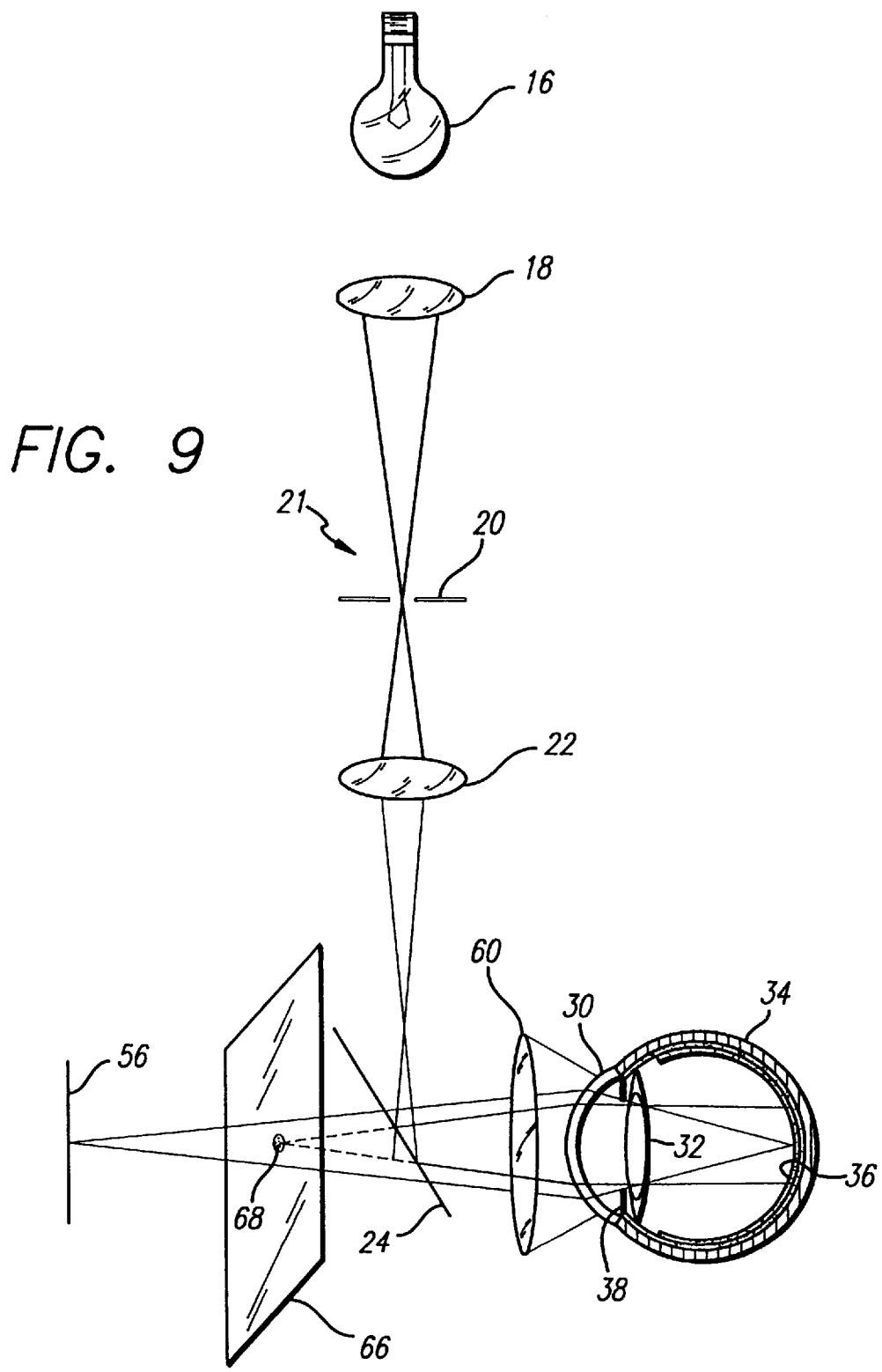
FIG. 9 is a schematic diagram, partially in section, of an embodiment of the invention illustrating the arrangement of optical elements necessary to modify the optical transform to provide a phase contrast image.

As depicted in FIG. 9, the system may also be arranged to provide a phase contrast image at the image plane 56. In this embodiment, the reflector 24 may be a pellicle beam splitter. Light incident on the beam splitter is transmitted into the eye 34 as described above. Light reflected out of the eye is transmitted through the beam splitter. A phase plate 66 having a semi-opaque dot 68 is disposed in the light beam scattered by the retina 36 along the viewing path. The semi-opaque dot 68 attenuates, but does not entirely block, the central maximum of the scattered light beam. The diameter and the degree of opacity of the semi-opaque dot 68 may be altered to enhance the contrast and resolution of the image of the retina 36 formed at image plane 56. All of the light passing through the phase plate 66, including the light that is attenuated by the semi-opaque dot 68, forms a modified optical transform that forms an image in the image plane 56. All of the internal structures of the eye 34 that may be viewed in the image plane 56, no matter what the size of the internal structure, will be shown in phase contrast.

In a preferred embodiment, the phase plate is a quarter wave plate. Other phase plates, such as, for example, one-eighth or one-sixteenth wave plates may also be used.

Figure 10:
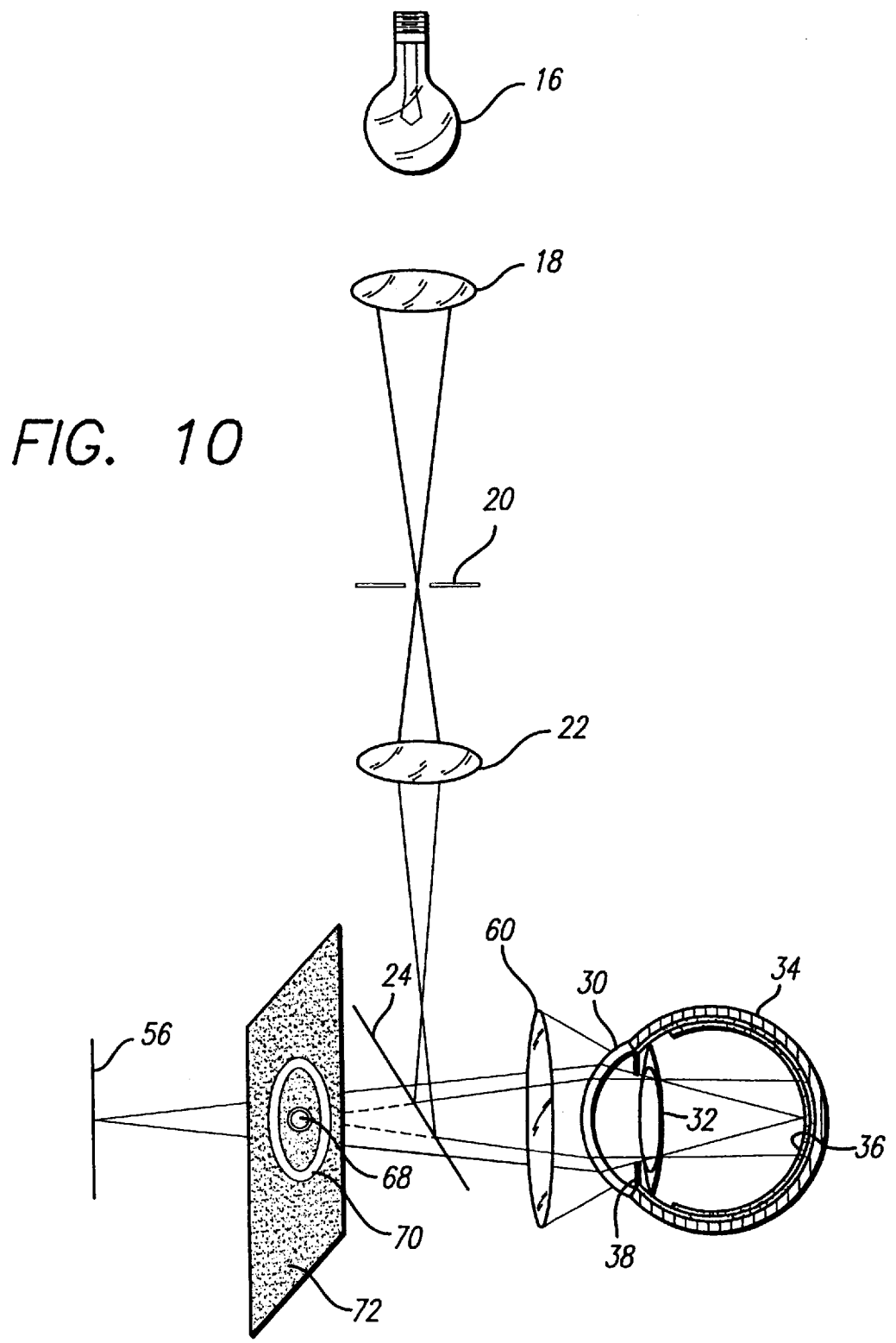
FIG. 10 is a schematic diagram of an alternative embodiment of the invention illustrating the arrangement of optical elements necessary to modify the optical transform to provide a fourier filtered image.

As depicted in FIG. 10, the embodiment described with reference to FIG. 9 may also incorporate fourier filtering of the images produced at the image plane 56 to further modify the optical transform of the image and enhance the analysis and visualization of transparent or translucent structures of the retina 36. In this embodiment, a plate 72 which is completely opaque except for a semi-opaque dot 68 disposed within an annulus 70 is positioned at the location of the real image of the spatial filter 20, as described above. As before, the semi-opaque dot 68 is sufficiently opaque to attenuate but not completely block the central maximum of the scattered light beam. This central attenuation area is surrounded by a totally opaque area which is in turn surrounded by annulus 70 forming fourier filter. The diameter of the annulus 70 which comprises the fourier filter may be controlled to allow light only from anatomical features of the retina 36 having a specific size to reach the image plane 56. Modification of the optical transform using fourier filtering in this manner provides the viewer with the ability to select and focus on a particular transparent or translucent structure of the eye 34 while obscuring other features that are of lesser interest to the viewer.

The plate 72 may also incorporate a phase filter such as is described with reference to FIG. 9. Combining the fourier filter with a phase plate in this manner provides the advantages of a phase contrast image of only those features of the internal structures of the eye 34 that have a selected size are shown.

Although only a single annulus 70 is shown in FIG. 10, a series of annuli separated by opaque areas of the plate 72 may also be used. Such a series of annuli allows the viewing of internal structures of the eye having discrete ranges of sizes to be viewed. For example, internal structures having sizes 0.01–0.02 mm and 0.05–0.07 mm may be viewed, while internal structures of the eye 34 having sizes of 0.03–0.04 mm may be obscured.

Figure 11:
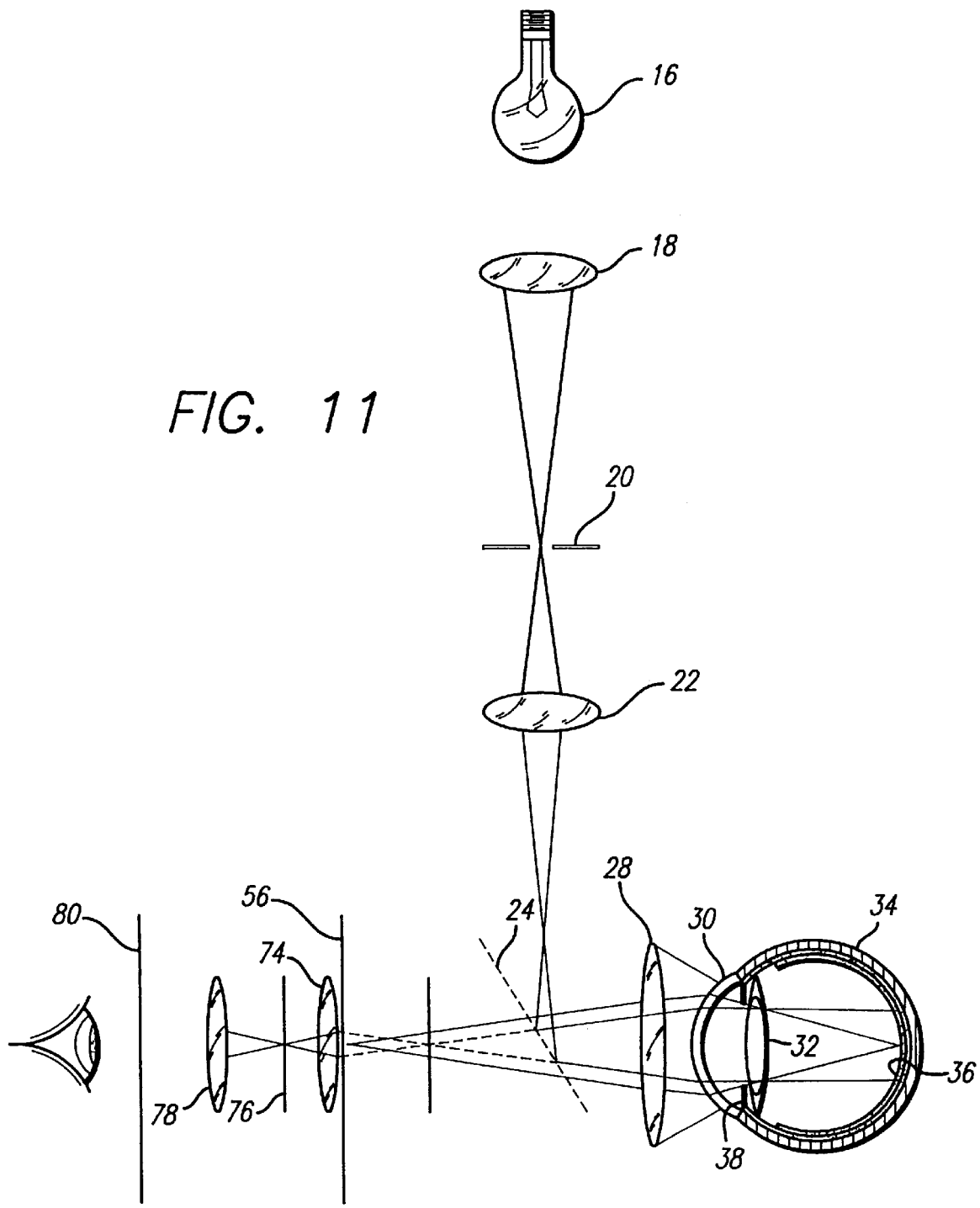
FIG. 11 is a schematic diagram showing relay lenses being used to form the optical transform in a different location to manipulate the transform plane at a different location within a beam of light reflected from internal structures of the eye.

The optical transform of the image of the retina 36 or other internal anatomical structures of the eye 34 may be further modified after formation of the first image at image plane 56 as depicted in FIG. 11. In this embodiment, the real image of the retina 36 or other internal structure of the eye is re-imaged by a lens 74 on to image plane 76. All of the methods described previously for altering the beam of scattered light beam prior to formation of the first image at image plane 56 may also be applied to alter the image formed at image plane 76. If necessary, the scattered light beam may be further focused by a lens 78 to form an image of the retina 36 in the image plane 80 that may be viewed by the observer 44.

As will be apparent to one skilled in the art, additional filters may be placed at many locations within the illumination system 12 and the viewing system 14 to further condition the illumination light beam and/or the scattered light beam. For example, polarizing lenses or gradient filters may be inserted into the light beams to take advantage of polarization effects to further enhance the images of the structures of the retina 36.

Figure 12:
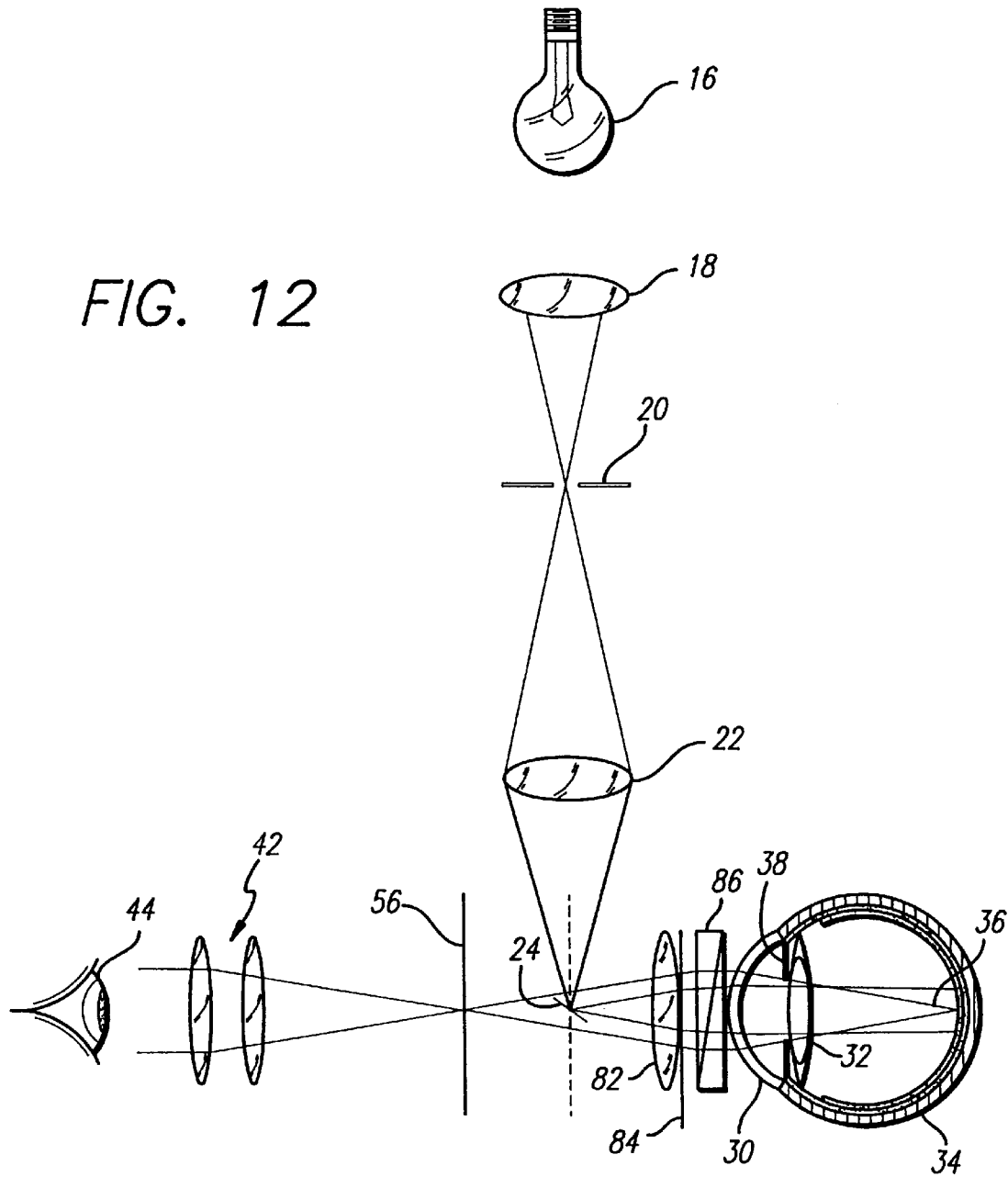
FIG. 12 is a schematic diagram of another embodiment of the invention depicting use of a polarizing lens, analyzer and wollaston prism to modify the optical transform.

A further embodiment of the system 10 that provides additional enhancement and visualization of the transparent and translucent structures of the eye 34 is depicted in FIG. 12. A polarizing lens 82, polarizer analyzer 84 and a wollaston prism 86 may be inserted into the optical path between the reflector 24 and the cornea 30 of the eye 34 to modify the optical transform of the image. The combination of the polarizing lens 82, the polarizer analyzer 84 and the wollaston prism 86 shear and unshear the light traversing through the combination of lenses and prisms to produce a lateral shear interference pattern in the image plane 56. This arrangement is advantageous in that it provides selective enhancement of those internal anatomical structures of the eye 34 that reflect or scatter light in a primarily specular manner. In contrast, images of structures of the eye 34 that reflect or scatter light in a primarily diffusive manner are not enhanced to the same degree, further aiding the selection and resolution of difficult to visualize structures of the eye 34. As described previously, the optical transform of the image using lateral shear interference may be further modified using the methods and apparatuses described above to combine the lateral shear interference pattern in the image plane with dark field, phase contrast, or fourier analysis.

While the figures depict a human observer viewing the final image provided by the system 10, it will be apparent to one skilled in the art that any electronic or photographic system could be used to capture the image. Moreover, the light source 16 is not limited to providing only light within the visible spectra. For example, a light source providing infrared light could be used to obtain infrared images of various structures of the eye, the images being modified by the optical systems described above to provide further resolution of translucent or nearly transparent structures of the eye 34. Moveover, the inventions described could also be used with the appropriate filters to perform fluorescein or indocyanine green angiography of the blood vessels of the retina 36.

Furthermore, the system may be constructed using interchangeable parts. In this manner, an observer may add additional filters or lenses, or substitute one type of lens or filter for another so that system 10 may be easily and rapidly configured to provide for increased resolution of retinal structures that are difficult, if not impossible, to visualize using prior art approaches.

While several forms of the invention have been illustrated and described, it will also be apparent that various modifications can be made without departing from the spirit and scope of the invention. Accordingly, it is not intended that the invention be limited, except by the appended claims.

I claim:

1. A diagnostic device determining the status of internal structures of the eye by analyzing light scattered out of the eye by the internal structures of the eye, comprising:

an transform generator adapted to receive the light scattered by the internal structures of the eye and to produce an optical transform of the scattered light;

a transform modifier adapted to modify the optical transform produced by the transform generator; and image forming means for forming an image of the internal structures of the eye from the modified optical transform.

2. The device of claim 1, further comprising image capture means for receiving the image from the image forming means.

3. The device of claim 2, wherein the image capture means comprises photographic means for forming an image photographically.

4. The device of claim 2, wherein the image capture means comprises electronic capture means.

5. The device of claim 2, further comprising:

a narrow bandwidth barrier filter disposed between the eye and the image capture means.

6. The device of claim 1, wherein the optical transform modifier comprises an optical element having an opaque area disposed in the second optical path, the opaque area obscuring a portion of the second optical path.

7. The device of claim 1, wherein the optical transform modifier comprises a quarter wave plate.

8. The device of claim 1, wherein the optical transform generator further comprises a fourier filter, the fourier filter obscuring light scattered by the structures having a predetermined range of sizes.

9. The device of claim 1, further comprising a fourier filter, the fourier filter obscuring light scattered by the internal structures of the eye having a predetermined range of sizes.

10. The device of claim 1, further comprising a light source for directing a beam of light into the eye.

11. The device of claim 10, wherein the light source comprises a source of sheared light; and wherein the image forming means comprises a means for unshearing the light scattered by the internal structures of the eye.

12. A device for examining the internal ocular anatomy comprising:

a light source adapted to produce a beam of sheared light and to direct the beam of sheared light into an eye along a first optical path, the beam of sheared light being scattered by ocular structures in the eye along a second optical path; and an analyzer disposed along the second optical path for receiving the scattered light from the eye, unshearing the scattered light and forming from the unsheared scattered light.

13. The device of claim 12, wherein the light source is adapted to produce a beam of laterally sheared light.

14. The device of claim 12, wherein the light source is adapted to produce a beam of radially sheared light.

15. The device of claim 12, further comprising capture means for receiving the image and for capturing and maintaining the image.

16. The device of claim 15, wherein the capture means comprises photographic means for forming a photograph of the received image.

17. The device of claim 15, wherein the capture means comprises electronic means for storing the image in a storage media.

18. The device of claim 12 wherein the light source comprises:

a polarizing lens that receives the beam of light and polarizes the beam of light; and a wollaston prism that receives the polarized beam of light and shears the polarized light.

19. The device of claim 12, further comprising:

a narrow bandwidth exciter filter disposed between light source and the eye; and a narrow bandwidth barrier filter disposed between the eye and the image capture means.

20. An apparatus for determining the status of internal structures of the eye, comprising:

illumination means for directing a beam of light into an eye to illuminate internal ocular structures of the eye;

shearing means disposed between the illumination means and the eye for shearing the beam of light;

unshearing means disposed external to the eye for unshearing light reflected out of the eye by the internal ocular structures;

an optical transform generator disposed between the unshearing means and the viewing means, wherein the optical transform generator produces an optical transform from the unsheared light; and a display adapted to form an image of the internal ocular structures from the optical transform.

21. A method for examining internal anatomical structures of an eye, comprising;

producing an optical transform of light reflected out of the eye;

modifying the optical transform of the reflected light;

viewing an image formed from the modified optical transform.

22. The method of claim 21, wherein the step of modifying the optical transform comprises obscuring a central area of the optical transform.

23. The method of claim 21, wherein the step of modifying the optical transform comprises applying a phase contrast filter to the optical transform.

24. The method of claim 21, wherein the step of modifying the optical transform comprises applying a fourier filter to the optical transform.

25. The method of claim 24, further comprising the step of applying a phase contrast filter to the optical transform.

26. The method of claim 21, wherein the step of modifying the optical transform comprises unshearing the beam of light reflected by the internal structures of the eye.

* * * * *